United States Patent [19]

Miwa et al.

[11] Patent Number: 4,580,451
[45] Date of Patent: Apr. 8, 1986

[54] ULTRASONIC SECTOR-SCAN PROBE

[75] Inventors: Hirohide Miwa, Kawasaki; Hajime Hayashi, Yamato; Takaki Shimura, Machida; Tadahiko Yanashima, Fujisawa; Kenji Kawabe; Atsuo Iida, both of Yokohama, all of Japan

[73] Assignee: Fujitsu Limited, Kawasaki, Japan

[21] Appl. No.: 735,300

[22] Filed: May 17, 1985

Related U.S. Application Data

[63] Continuation of Ser. No. 476,720, Mar. 18, 1983, abandoned.

[30] Foreign Application Priority Data

Mar. 20, 1982 [JP] Japan .................. 57-45395
Mar. 20, 1982 [JP] Japan .................. 57-45396

[51] Int. Cl.$^4$ ............................. G01N 29/00
[52] U.S. Cl. ............................. 73/626; 73/642; 128/660
[58] Field of Search .............. 73/626, 642, 644; 128/660

[56] References Cited

U.S. PATENT DOCUMENTS

| | | | |
|---|---|---|---|
| 3,245,251 | 4/1966 | von Ardenne | 73/642 |
| 3,881,164 | 4/1975 | Kossoff | 73/642 |
| 4,183,249 | 1/1980 | Anderson | 73/642 |
| 4,204,435 | 5/1980 | Bridoux et al. | 73/626 |
| 4,281,550 | 8/1981 | Erikson | 73/626 |
| 4,340,944 | 7/1982 | Dory | 73/642 |

FOREIGN PATENT DOCUMENTS

| | | |
|---|---|---|
| 2727256 | 12/1977 | Fed. Rep. of Germany . |
| 3008553 | 9/1980 | Fed. Rep. of Germany . |
| 2367289 | 5/1978 | France . |
| 2091520 | 7/1982 | United Kingdom ............ 73/626 |

Primary Examiner—Stewart J. Levy
Assistant Examiner—John E. Chapman, Jr.
Attorney, Agent, or Firm—Staas & Halsey

[57] ABSTRACT

An ultrasonic sector-scan probe comprises at least an array having a plurality of ultrasonic transducer segments, a window for transmitting and receiving ultrasonic waves and an ultrasonic wave propagation medium filled in a front space between the array and the window. A group of the ultrasonic transducer segments are selectively driven as an aperture and ultrasonic waves emitted therefrom are converged into a beam for transmission and reception. By partly or entirely changing the segments in the group with the ones outside the group the scan line is shifted to a new angle, and a member under test contacted with the window on the outside thereof is sector-scanned by the ultrasonic beam. The array is arranged so that scanning lines of the groups intersect at one point in the window or in its vicinity for sector scan. An acoustic lens is provided in the window or in its vicinity so that the ultrasonic beam may be converged over the measuring depth range of the member under test with or without phase control of the segments in the group. Furthermore, the array is arranged multidimensionally or in plural linear arrays so that the scanning lines of the groups intersect substantially at one point in the window or in its vicinity for sector scan, thereby performing sector scan of at least two sections and/or three-dimensional sector scan.

2 Claims, 18 Drawing Figures

FIG.12
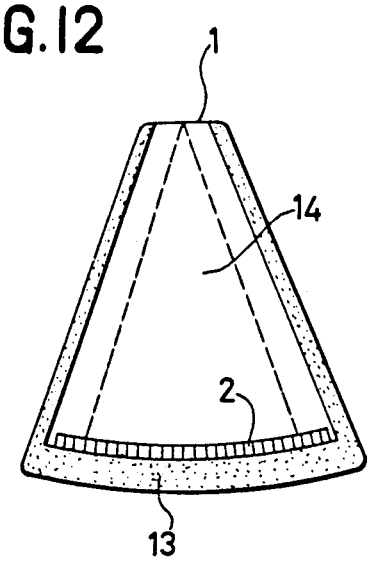
FIG.13A
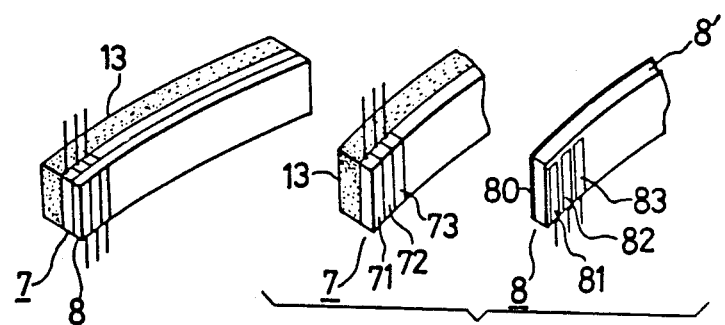
FIG.13B
FIG.14
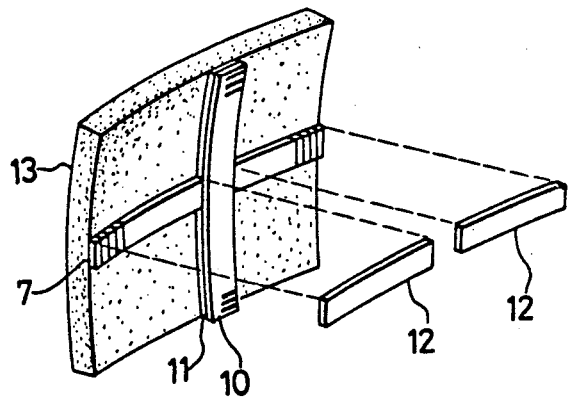

FIG.15A
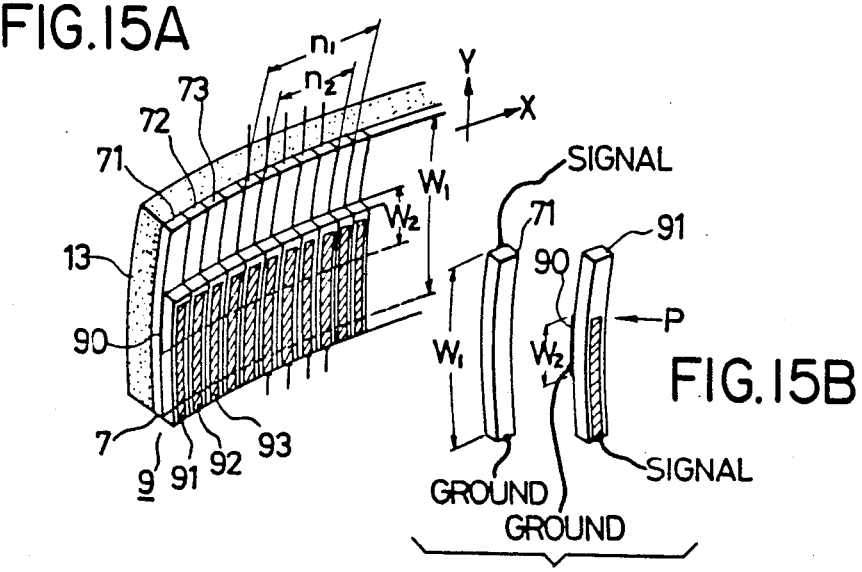
FIG.15B
FIG.16
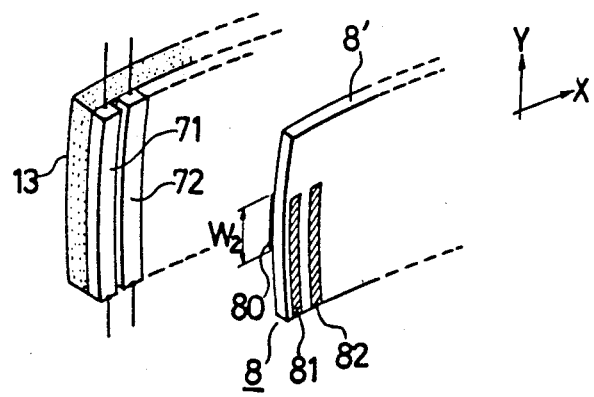

ULTRASONIC SECTOR-SCAN PROBE

This is a continuation of co-pending application Ser. No. 476,720 filed on Mar. 18, 1983, now abandoned.

BACKGROUND OF THE INVENTION

The present invention relates to a measuring apparatus which emits an ultrasonic beam to a medium under test and which utilizes the reflected wave therefrom in medical diagnosis, nondestructive testing and so forth and, more particularly, to an ultrasonic sector-scan probe which emits an ultrasonic beam fanwise from its position held in contact with the medium under test for observing its interior.

The sector scan of an ultrasonic beam has the advantage that the interior of a living tissue, for example, can be observed over a wide field from one small contact portion. Especially, for observing a heart or the like, the sector scan is exclusively employed because an appreciable area of the heart can be observed by contacting a probe having a narrow portion between pairs of ribs, for avoding the obstacles presented by the ribs.

The sector-scan techniques heretofore employed are roughly divided into a mechanical scan method which drives a focused ultrasonic beam to scan fanwise by mechanically wobbling or rotating a disc-shaped or rectangular, concave, piezoelectric transducer, and a phased array type electronic scan method in which a number of narrow rectangularly shaped piezoelectric segments are arrayed, wherein the temporal phases for driving the elements for transmission are controlled and received signals are also controlled in their temporal phases and added together, thereby to electronically deflect the directions of transmission and reception.

The mechanical scan method is highly advantageous in that it is simple, inexpensive and excellent in beam performances, such as in the beam directivity pattern, intensity and frequency spectrum and such as in the direction/magnitude of a side lobe, and in that these beam performances do not vary with the angle of deflection. With this method, however, owing to mechanical inertia, the scanning must be effected in a sequential order and cannot be jumped non-sequentially to a desired scanning line.

In contrast thereto, the phased array type electronic scan method permits such an arbitrarily jumping scan but necessitates the complex and bulky circuit arrangements for phase control, and hence is very expensive. Also it is inferior in the beam performances to the mechanical scan method, and the abovesaid performance of the beam undergoes substantial changes with the angle of deflection. Furthermore, this method possesses the defect that a grating side lobe resulting from an array construction exerts a bad influence upon measurement.

In FIG. 1, 3-1 shows a system proposed by ALOKA LIMITED (Japanese Utility Model Application Publication No. 41267/77) and 3-2 shows a system proposed by HOFFMAN la ROCHE LTD. (Japanese Patent Application Publication No. 36942/81) for obviating the aforementioned drawbacks. In FIG. 1, reference numeral 1 indicates linearly arrayed ultrasonic transducer segments on a circular arc; 2 designates the intersection point of scanning lines; 3-1 and 3-2 identify apertures formed of corresponding segment groups; 4 donotes an acoustic window; and 10 represents a front space room. In this system, the scanning is performed by shifting the location of the operated group in the arrayed segments. The linear array of transducer segments that is well known for abdomen diagnosis is rearranged on an arcuate, concave and circular arc and the focussing point of the beam provided by the aperture comes to the center of the circular arc in the case of 3-1, which is set on the contacting window of the probe with the member under test or in its vicinity. The beam scanning is effected by simple change-over control of the segments instead of by phase control, so that this system is simple and inexpensive. Besides, although the grating lobe cannot be removed, the beam performances are excellent and have no deflection angle dependence. In this system, however, the piezoelectric segments forming the transducer array 1 and the window 4 which contacts the member under test, such as the human body or the like, for transmitting thereinto ultrasonic waves and receiving therefrom reflected waves, must be spaced apart an equal distance to the radius of curvature of the circular arc, and the space defined between the array 1 and the window 4 (which space will hereinafter be referred to as the front room 10) must be filled up with a medium that conducts ultrasonic waves. Furthermore, in order to avoid the influence of what is called multiple reflection, that arises from re-reflection and re-radiation of reflected waves between the window 4 or the skin surface and the piezoelectric array, it is necessary to make substantially equal the propagation time of ultrasonic waves in the front room 10 and the propagation time of ultrasonic waves in a range to be measured in the member under test. According to the above-mentioned prior art, in the case where water is used as the medium filling up the front room 10, since the speeds of sound in water and in the living tissue are nearly equal to each other, the path length in the front room, that is, the radius of curvature of the circular arc of the concave array, must be almost the same as the range to be measured (about 18 cm in the case of a heart or the like). Accordingly, the probe used is very bulky. The overall angle of scanning in the front room 10 (equal to the angle subtended at the center of curvature by the circular arc) becomes equal to the overall angle of scanning in the living body (90° in the case of a heart or the like). In consequence, the angle of the front end of the probe exterior which probe includes its container and a sound absorber, becomes almost 100°, making it difficult to incline the direction of the center of the fan-wise scanning between the ribs. Moreover, the beam pattern is defined only by the aperture defined by the group 3-1; namely, the beam diameter decreases, from that of the aperture formed by the segment group 3-1, towards the center of curvature of the circular arc, is a minimum at the center of curvature and then increases point-symmetrically with respect to the center of curvature. At the deepest range in the member under test, the beam diameter is substantially equal to the diameter of the aperture. Accordingly, the degree of convergence of the beam is very low. To obviate such a defect, it has been proposed by HOFFMAN la ROCHE LTD. as noted above to perform focussing by the aperture segment group 3-2 in FIG. 1 electronically. The focus point of the scanning beam formed by the aperture of segment group 3-2 is not limited specifically to the vicinity of the window 4, unlike the case of the scanning beam formed by the aperture of segment group 3-1. By controlling the phases of driving for each segment in the group and the phases of reception, the convergence of the beam is electronically weakened so that the focus point, which in the case of 3-1 is geometrically set to the center of curvature of the circular arc, can be moved to a farther position, for instance, at a position two-thirds of a maximum depth of measurement (indicated by $0_1$), thereby resulting in better beam convergence throughout the range. As will be appreciated from FIG. 1, however, in the system 3-1 above proposed by ALOKA LIMITED, since the beam diameter at the window 4 is sufficiently reduced, the width of the window 4 can be made small, whereas in the above system 3-2 proposed by HOFFMAN la ROCHE LTD. the beam diameter at the window 4 is large and the width of the window 4 can not be made small. This is disadvantageous for the sector scan which is mostly used for diagnosing a heart from a narrow gap between the ribs.

In practice, there exists, in addition to the beams shown in FIG. 1 which can be handled by acousto-optics, a diffusive beam which is to be superimposed on the abovesaid beam and which linearly spreads out at a vertex angle of 2 times 0.6 $\lambda/a$ radian, where a is the half-width of an aperture of the group and $\lambda$ is the wave length of the ultrasonic waves used. This is common to both systems described above in respect of FIG. 1, and the width of this beam is larger than or substantially equal to the width of the acousto-optical beam in the focal and farther regions, but no consideration is paid to this beam in either prior art.

In the HOFFMAN la ROCHE LTD. prior art above there is further proposed a method of permitting scanning at a one-half pitch of the segment pitch and a method of beam focusing in a perpendicular direction to the sector scan plane. Since such methods are well-known in the conventional linear array of a probe for diagnosing the abdomen, no further description will be given hereafter. In this prior art it is further proposed to use, as the medium in the front room, a medium in which the speed of sound is lower than in water. This makes it possible to obviate the defect that the probe proposed in the aforementioned Japanese Utility Model Application Publication No. 4126/77 of the first prior art system 3-1 above is very bulky. The media specified in this prior art include certain biological liquids and silicone rubber, the speed of sound in which is about 1000 m/sec. Since the speed of sound in water and the living body is approximately 1500 m/sec, the path length in the front room above is about ⅔ that of this prior art, and the size of the probe and the angle of scan can be reduced to substantially ⅔ those in the utility model gazette. From a practical point of view, however, the measurement depth range is 18 cm and the overall angle of scanning is 90°, for instance, in diagnosing a heart. However, with the probe of HOFFMAN la ROCHE LTD above, the path length in the front room 10 can be 12 cm and the overall angle of scanning is about 60°, while the probe, including the sound absorber and the container wall, is still too large for practical use. This is understood to be one reason why the prior art system 3-2 above has not provided a practical system.

FIG. 2 illustrates the state of applying an ultrasonic fan-shaped probe in a tilted condition. Reference numeral 1 indicates a linear array; 2 designates the intersection of scanning lines; 7 identifies a sound absorber and container; 8 denotes the surface of the body (or the skin surface); and 9 represents an internal organ near the skin surface. In view of the length of the prior art teaching of the probe above the 12 cm path length in the front room 10 is sufficient for practical use but the 60° overall angle of scanning in the front room 10 is too large. That is, as shown in FIG. 2, in order to observe the organ 9 (for example, the right atrium or the right ventricle of the heart) near the skin surface over a wide visual field, it is desirable to tilt the fan-shaped probe, so that the most deflected scan line almost coincides with the skin surface 8 as shown. In this case, the center line 1 of the probe forms an angle $\theta_2$ with the skin surface 8 and the angle of scanning in the front room is $\theta_1$ on either side of the center line 1. Accordingly, a marginal angle $\alpha$ for tilting with respect to the skin surface 8 is $\theta_2-\theta_1$. In practice, an additional angle other than $\theta_1$ is involved, which arises due to the sound absorber 7, the container and the marginal room around the fan-shaped space in the front room 10. Consequently, it is necessary that $\theta_2-\theta_1$ be larger than 20°. In the case where $2\theta_2=90°$ and $2\theta_1=60°$, the marginal angle $\alpha$ for tilting is $\theta_2-\theta_1=15°$, which is insufficient for practical use.

Furthermore, since only one tomographical section is obtained with the prior-art ultrasonic sector-scan probes, no accurate geometrical orientation with respect to an organ can be effected. For instance, the heart always pulsates and also shifts and rotates three-dimensionally as a whole owing to breathing. Accordingly, with the observation of only one section, it is unclear which part of the heart is scanned. To solve this problem, it is customary in the prior art to make observations of desired sections in sequence while changing the posture of the probe with respect to the examinee's body and while turning the probe by 90° around its axis. In this case, since the probe is manually rotated, it is very difficult to retain geometrical accuracy with each change of the posture of the probe.

It is considered that this problem could be solved by mechanically holding the probe in a fixed posture. However, this prevents breathing and hence is undesirable, and it has not been employed at all.

Another solution heretofore proposed is to mechanically turn the probe by 90° around its axis while manually holding its outer container in a fixed posture with respect to the examinee's body. But this method is disadvantageous in that the probe used is bulky, and in that measurement errors are still large because it is difficult to manually hold the probe container in a completely fixed posture, because different sections are not concurrently observed and because much time is needed for rotating the probe.

Apart from the present invention, the present inventor has proposed a method of observing two sections simultaneously with two probes while at the same time detecting their relative positions with angle detectors mounted on the joints of their linkage arm, thereby to enable three-dimensional but accurate observations.

In this case, however, two probes are used and they must contact with the examinee's body at two places. Generally, in the cases of middle-aged or younger persons, two contact areas effective for the examination of the heart can be found but, as for aged persons, only one effective contact area can be found in many cases, and the successful cases involve 40 to 50% of examinees of all ages.

In view of the above, there is a strong demand for the realization of a system for electronically switching two or more different sections at high speed or for observing them simultaneously through one contact area, but such a system has not been reported yet.

Usually the electronic sector scan is performed using a phased array. For this sector scan, there has also been proposed by the present inventor to arrange two phased arrays in laminated layers for scanning perpendicular sections so that each sector scan plane perpendicularly intersects the other, for instance. In this case, the individual sections can be observed simultaneously by using different frequencies for them.

However, the fabrication of such a double-layer phased array is complex and the phase control circuit is also complex and expensive.

SUMMARY OF THE INVENTION

It is therefore an object of the present invention to provide a sector-scan probe the window of which is small even if a transducer array is a circular arc-shaped linear array, and which is capable of providing a narrow beam in the material under test.

Another object of the present invention is to provide an electronic sector-scan probe which is small in width of the window, small in beam diameter and excellent in various beam performance as compared with the conventional phased array type system and which permits jump scanning and simple and inexpensive scanning control.

Another object of the present invention is to provide a sector-scan probe in which the width of the window and the path length $l_1$ in the front room can be reduced and which is therefore small in size and can be tilted sufficiently over a wide angular range.

Another object of the present invention is to provide a sector-scan probe in which a plurality of linear or planar transducers are provided in a front room with a single window so that the scanning the lines formed by any segment group may intersect substantially at one point near the window, by which it is possible to form a plurality of different sector-scan planes while holding the probe in a certain posture at one contact area with the member under test.

Yet another object of the present invention is to provide a three-dimensional sector-scan probe which is accurate, easy to handle and inexpensive.

In accordance with objects of the present invention, the ultrasonic sector-scan probe is devised of an array comprising a plurality of ultrasonic transducer segments, a window for transmitting and receiving ultrasonic waves and an ultrasonic propagation medium filled in a front room defined between the array and the window. Some plural adjacent transducer segments in the array are selectively driven as one group and ultrasonic waves emitted therefrom are formed into a beam for transmission into the member held in contact with the window on the exterior thereof. Then reflected waves from the member are again received by the group through the window. Then, by partly or entirely changing the selected segments of the group with other segments in the array, the group location is shifted to produce a new scan line. The segments are arrayed so that scanning lines formed by any selectively grouped segments may all intersect substantially at one point in the window or in its vicinity to perform sector scan in the member, and an acoustic lens is provided in the window or in its vicinity so that an ultrasonic beam focusing zone may be formed over the measuring depth range of the member under test.

In accordance with other objects of the present invention, the ultrasonic three-dimensional sector-scan probe is devised of arrays comprising a plurality of ultrasonic transducer segments, a window for transmitting and receiving ultrasonic waves, and an ultrasonic propagation medium filled in a front room defined between the arrays and the window. Some transducer segments in the array are grouped and selectively activated as an aperture and ultrasonic waves emitted therefrom are formed into a beam for transmission to the material held in contact with the window on the outside thereof and then reflected waves from the subject are received by the group through the window. By partly or entirely changing the selected segments of the group with other segments in the array, the group location in the array is shifted to produce a new scan line. The segments are arrayed multidimensionally or in plural linear arrays; so that scanning lines formed by any group may all intersect substantially at one point in the window or in its vicinity to perform sector scan in the member. The plural arrays or the multidimensional array provide a sector scan of at least two sections and/or a three-dimensional sector scan.

BRIEF DESCRIPTION OF THE DRAWINGS

FIG. 12 is a diagram illustrating a specific example of the construction of the probe depicted in FIG. 9;

FIGS. 13A and B illustrate a specific example of the structure of the transducer array in a probe of the present invention which employs laminated linear arrays;

FIG. 14 is a diagram illustrating a specific example of the structure of the arrays in a probe of the present invention which employs two perpendicularly intersecting double layer linear arrays; and FIGS. 15A and B and 16 are diagrams illustrating specific examples of the structure of the array in the case of performing aperture control in the probe of the present invention.

DETAILED DESCRIPTION OF THE PREFERRED EMBODIMENTS

Figure 3:
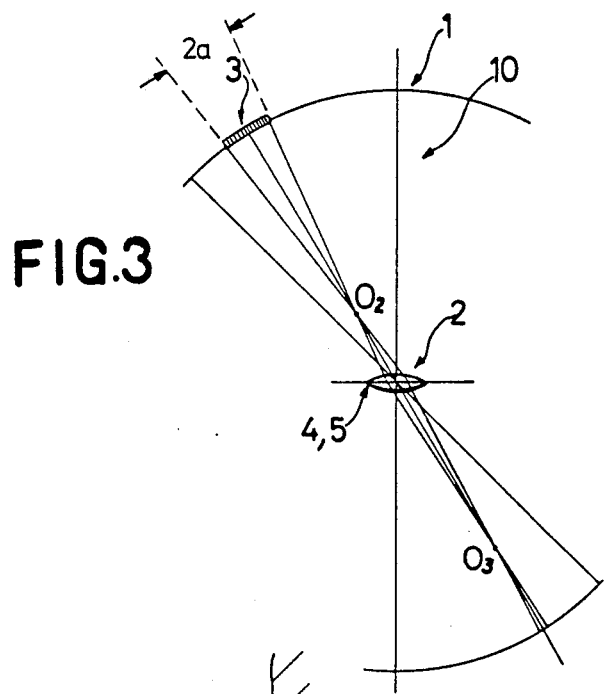
FIG. 3 is a diagram illustrating an embodiment of the ultrasonic sector-scan probe of the present invention.
Figure 5:
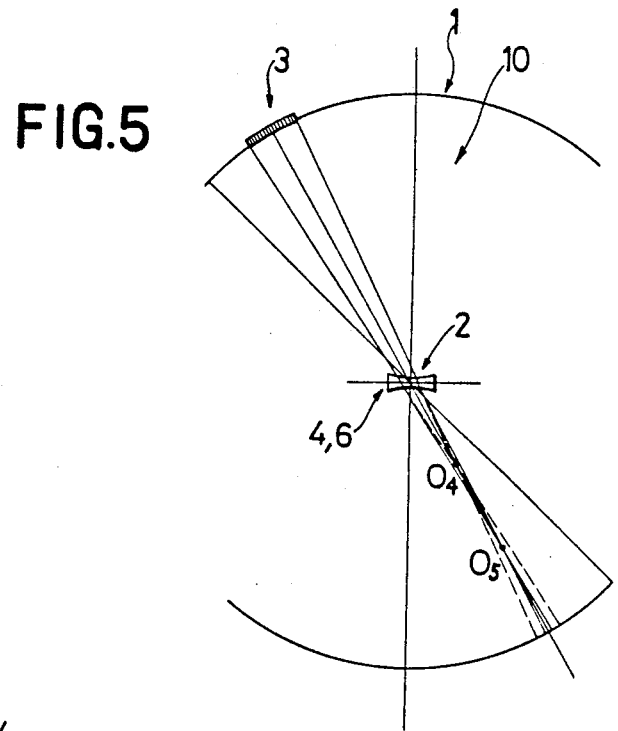
FIG. 5 is a diagram illustrating another embodiment of the ultrasonic sector-scan probe of the present invention.
Figure 7:
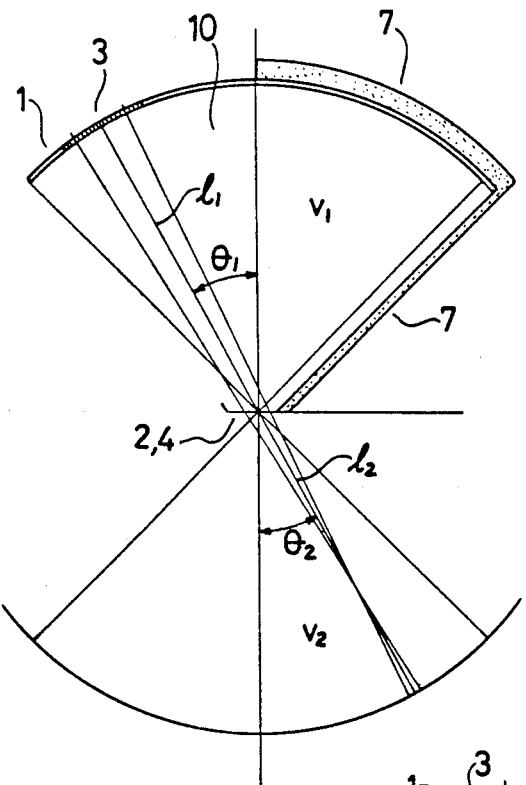
FIGS. 7 and 8 are diagrams explaining the effect of the speed of sound of a medium in the front room.

FIG. 3 illustrates an embodiment of the ultrasonic sector-scan probe of the present invention; FIG. 5 illustrates another embodiment of the present invention; and FIG. 7 is explanatory of the effect of the speed of sound of the medium in the front room of the ultrasonic sector-scan probe. In FIG. 5, reference numeral 1 indicates a linear array of ultrasonic transducer segments arrayed on a circular arc, 2 designates the intersection point of scanning lines, 3 identifies an aperture provided by a segment group, 4 denotes a window, 5 represents a converging lens, 6 shows a diverging lens, 7 refers to a sound absorber and 10 signifies a front space or room.

A description will be given, with reference to FIG. 3, of an embodiment of the present invention which uses an acoustic lens. The linear array 1 may be constructed with narrow rectangular-shaped piezoelectric segments arranged side by side on a circular arc. A suitable number of segments are selected as one group in the linear array and these selected segments are driven. The ultrasonic waves emitted therefrom generate a converging beam. The segment group 3 is selected as an aperture and has an opening width $2a$. The segments that are farther from the center of the group are operated in earlier temporal phases than the segments that are nearer to the center, for transmission and reception. By this temporal phase control for each segment in the group, the aperture operates as if the radius of curvature is reduced. By such additional electronic convergence of the ultrasonic waves, the focus point is formed at a point $0_2$ in the front room 10 closer than the intersection point 2 of scanning lines which is the geometrical center of curvature of a circular arc. In FIGS. 3 to 7, the window 4 is placed at the position of the intersection 2 of the scanning lines and the converging lens 5 is provided in the window 4. The converging lens 5 itself can be used as the window 4. When the material of the converging lens 5 is silicone rubber or the like, the speed of sound of which is lower than the medium surrounding the lens 5, it corresponds to an optical lens with a refractive index which is larger than 1. Accordingly, a convex lens is needed for converging a beam. Conversely, in the case where the converging lens 5 is made of polystyrene or the like, the speed of sound which is higher than the surrounding medium, the converging lens 5 is concave as in FIG. 5. By the converging lens 5 of FIG. 3, the diverging ultrasonic beam beyond the focus $0_2$ can be focused again at a suitable position $0_3$ in the member under test, for example, at a point $\frac{2}{3}$ a maximum measurement depth. As the point $0_2$ approaches the intersection point 2 of the scanning lines, the beam width can be made smaller but the design of the converging lens 5 becomes difficult, so that the point $0_2$ has an appropriate value. It will be evident from comparison of the beam width in FIG. 3 with the system 3-2 in FIG. 1, that the beam width at the window 4 in FIG. 3, that is, at the converging lens 5, is smaller than the one of system 3-2 in FIG. 1 and a final focus point is formed at the same point as in FIG. 1. Consequently, the beam width in the member under test near the window 4 is also smaller. Furthermore, as described previously, a diffusive beam, which diverges linearly as travelling from the center of the aperture with the diverging angle noted above of two times $0.6 \lambda/a$ radian, where $\lambda$ is the wavelength of the ultrasonic waves a is the half-width of the aperture, is superimposed on the abovesaid acousto-optical beam, though not shown. The curvature of the circular arc and the convergence by electronic temporal phase control have no effect on this diffusive beam. Accordingly, the case of both FIGS. 1 and 3, once the aperture width $2a$ is determined, substantially the same diffusive beam is produced. The window 4 shown in FIG. 1 has no effect on this diffusive beam but, in FIG. 3, the converging lens 5 functions to effectively converge also the diffusive beam, and the diameter of the diffusive beam in the member under test can be reduced.

Figure 4:
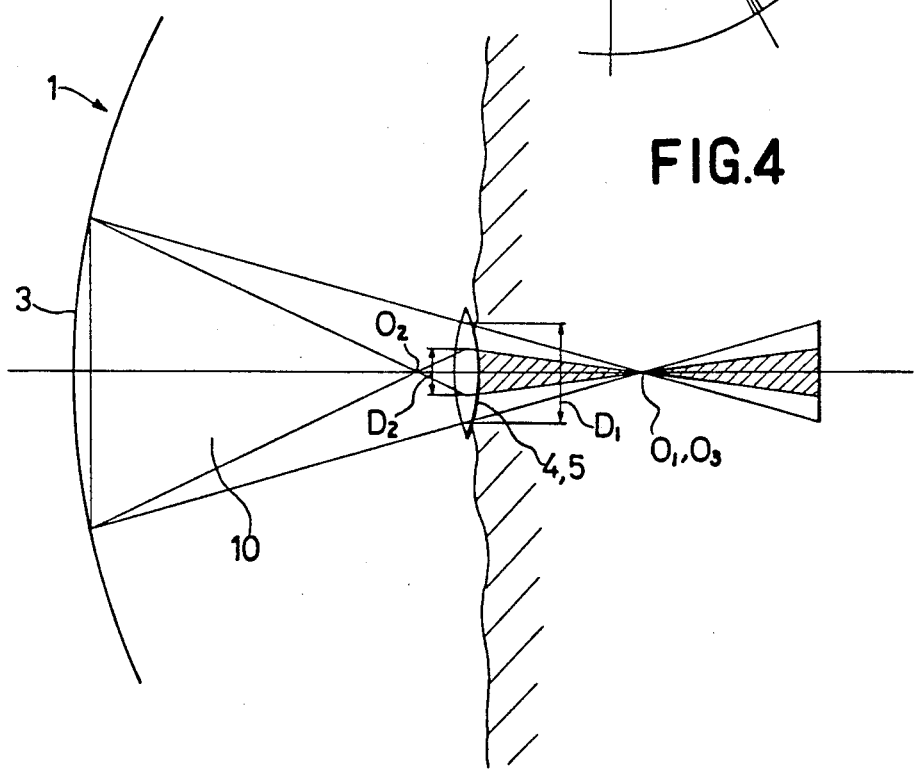
FIG. 4 is a diagram explaining how the window can be made smaller according to the embodiment of FIG. 3.

FIG. 4 explains how the window 4 can be made smaller according to the embodiment of the present invention illustrated in FIG. 3. In the absence of the converging lens 5, ultrasonic waves emitted from the aperture 3 and converging on the point $0_1$ in the subject have a beamwidth $D_1$ in the window 4 as shown but, in the case where the converging lens 5 is used according to the present invention, the ultrasonic waves from the aperture 3 are focused on the point $0_2$ in the front room 10 and then converged again by the coverging lens 5 on the point $0_3$, so that the beam width $D_2$ in the window 4 can be smaller than in the case where the converging lens 5 is not employed.

Referring now to FIG. 5, another embodiment of the present invention will be described which employs an acoustic lens. In contrast to the embodiment of FIG. 3, a diverging lens 6 is provided in the window 4 or as the window itself. By focussing the beam from the aperture (segment group) 3 on a position $0_4$ not so far from the intersection point 2 of the scanning lines, the beam width in the window 4 is reduced. In this case, since the beam having passed through the position $0_4$ diverges to become wider, the focus point is shifted by the diverging lens 6 to a farther position $0_5$, for example, to a position $\frac{2}{3}$ of a maximum measurement depth. By this arrangement, the beam width in the window 4 can be made smaller than in the case of 3-2 in FIG. 1 and the beam width before and after the converging point $0_5$ in the member under test can also be reduced. In this case, however, the diffusive beam is further diverged by the diverging lens to have a larger beam width in the member in contrast to the embodiment of FIG. 3. To avoid this, it is necessary to prepare a sufficiently large aperture $2a$ to make the divergence angle small in the initial design.

Figure 6:
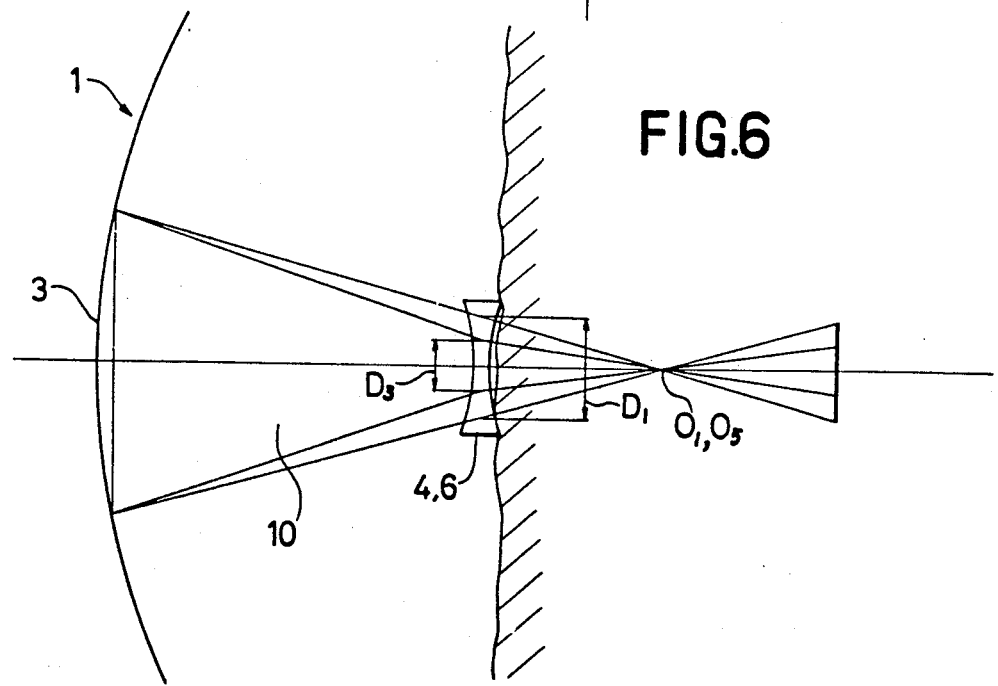
FIG. 6 is a diagram explaining how the window can be made smaller according to the embodiment of FIG. 5.

FIG. 6 explains how the window can be made smaller according to the embodiment of FIG. 5. of the present invention. In FIG. 6, when the diverging lens 6 is not used, the ultrasonic waves emitted from the aperture 3 and focussing on the point $0_1$ in the member under test have the beam width $D_1$ as shown. On the other hand, when the diverging lens 6 is used according to the present invention, the ultrasonic waves from the aperture 3 are diverged by the diverging lens 6 and focused on a point $0_6$ in the member, so that the beam width $D_3$ in the window 4 can be made smaller than in the case where the diverging lens 6 is not employed.

Figure 1:
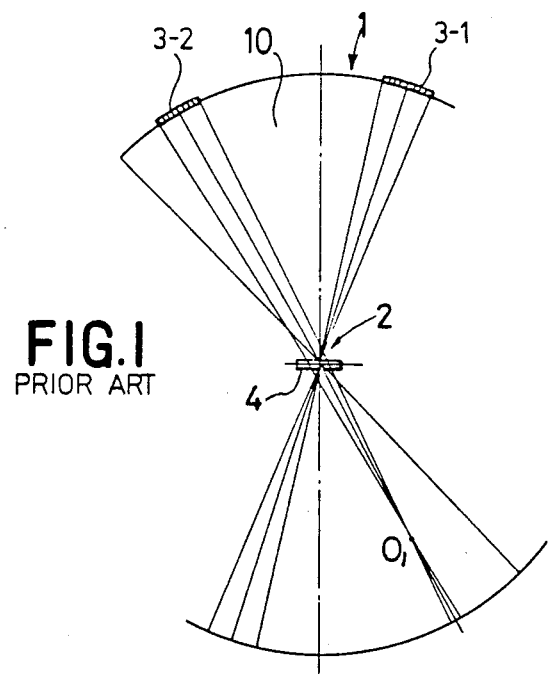
FIG. 1 is a diagram schematically showing prior art ultrasonic sector-scan probes based on a circular arc linear array.
Figure 2:
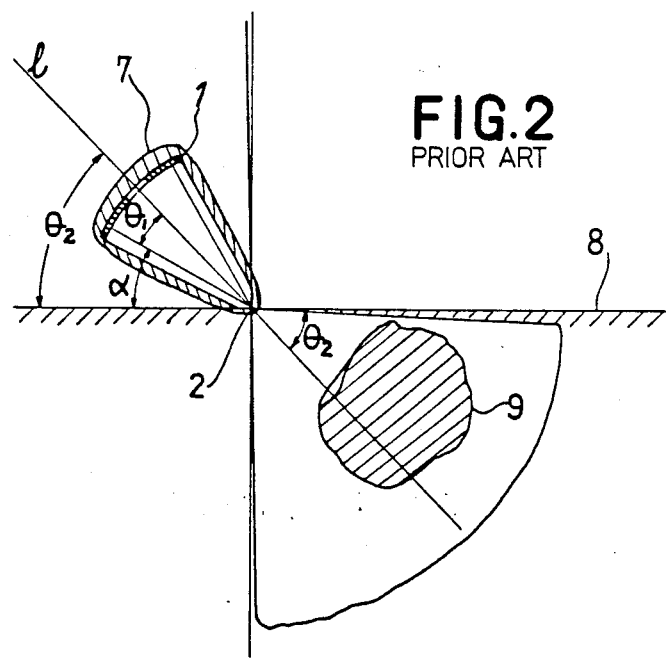
FIG. 2 is a diagram schematically showing the state in which the ultrasonic sector-scan probe is applied in a tilted posture.

Also in the system 3-1 of FIG. 1 in which the beam focussing point agrees with the position of the window 4 (proposed by ALOKA LIMITED) as noted above, it is theoretically possible to carry into practice the present invention described above in respect of FIGS. 3 and 5 by providing a diverging lens immediately inside the focus point or a converging lens immediately outside the focus; but it is somewhat difficult to design the lenses.

It is evident that in the case where the scanning lines intersect each other in the window and the beam width is small, the width of the window can be minimized. It is also possible to employ conventional dynamic focussing control for reception in combination with the present invention, when a much smaller beam width can be obtained.

Figure 8:
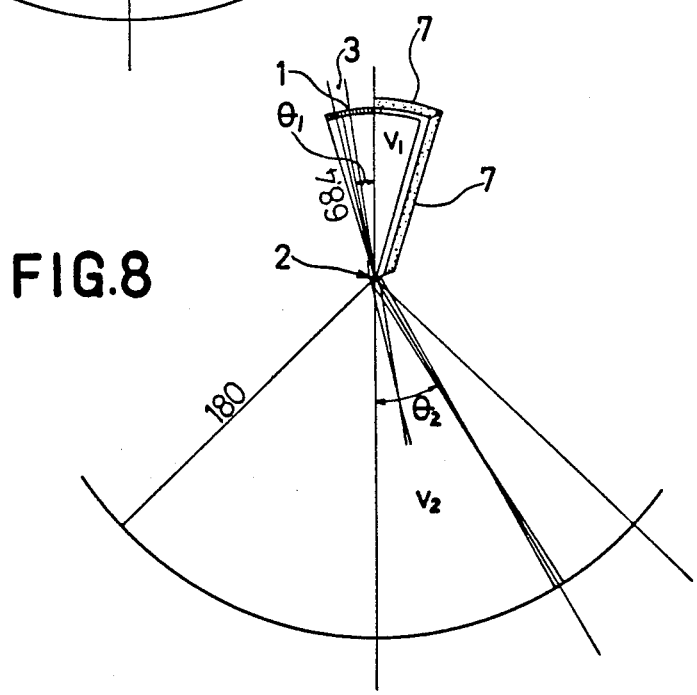

As described above, according to the embodiments of FIGS. 3 and 5, the width of the window can be made smaller and the beam width can also be made narrower over the entire range of the measurement depth. However, these embodiments are disadvantageous in that they require the front room because the scanning lines of the conventional linear array are rearranged in a circular arc to intersect for the sector scan. Turning next to FIG. 7, the effect of the sound speed of the medium in the front room will be described. For preventing multiple reflection between te array 1 and the window 4, the following condition is necessary:

$$l_1/v_1 \geq l_2/v_2$$

where $l_1$ is the distance between the window 4 and the array 1, $v_1$ is the speed of sound of the medium in the front room 10, $l_2$ is a maximum measurement depth of the member held in contact with the window 4 on the outside thereof and $v_2$ is the speed of sound in the member under test. In the case of examination of a heart, $l_2=18$ cm, so that when $v_1=v_2$, $l_1$ also becomes 18 cm, resulting in the probe becoming too long to use. Furthermore, as shown in FIG. 8, a scanning line incident on the window 4 at an incidence angle $\theta_1$ with reference to the normal of the window 4 is refracted at the window 4 when $v_1 \neq v_2$, and emerges out of the window 4 at an angle $\theta_2$. In this case, according to the Snell's law, the following relation holds:

$$\sin\theta_1/\sin\theta_2 = v_1/v_2$$

If $v_1$ is approximately equal to $v_2$, then $\theta_1$ is approximately equal to $\theta_2$. In the examination of the heart or the like, it is desirable that $2\theta_2=90°$, and consequently $2\theta_1$ is approximately equal to 90°. Accordingly, the aforementioned tilting margin, $\alpha=\theta_2-\theta_1=0$, is unsatisfactory. This can be solved by using a medium in the front room, the speed of sound $v_1$ of which is equal to or lower than the speed of sound $v_2$ in the member under test. In a living body, the speed of sound $v_2$ is 1538 m/sec, so that if the speed of sound $v_1$ is 1000 m/sec in the system 3-2 noted above, then $l_1=12$ cm and $2\theta_1=60°$; but these values are still insufficient for practical use. It is desired that $v_1/v_2 \leq \frac{1}{2}$. Fortunately, fluorinated oils have speeds of sound such as 700 m/sec, 527 m/sec and 590 m/sec, and are commercially available, for instance, under the trade names FO48, FO72 and FO75 by 3M Inc., and the use of these oils satisfies the condition $v_1/v_2 \leq \frac{1}{2}$. Accordingly, assuming that $v_1=590$ m/sec, $v_1/v_2=0.38$. This example is shown in FIG. 8, in which $l_1=6.84$ cm, $2\theta_1=32°$ and $\alpha=\theta_2-\theta_1=29°$. From comparison of FIG. 7 showing an example of $v_1$ being approximately equal to $v_2$ and FIG. 8, it is seen that the probe is reduced in size and the tilting margin a is increased.

It is self-evident by analogy from ordinary optics that the present invention described previously in respect of FIGS. 3 and 5 is also applicable to the case of $v_1 \leq v_2$. This can be achieved by changing the design constant of the lens. In the case of $v_1 < v_2$, a special lens need not always be used but the window may also be made to serve as the diverging lens or as the converging lens by forming it to be concave or convex. While in the foregoing explanation, a single arc-shaped linear array is used, plural arc-shaped linear arrays and spherically shaped matrix planar array can similarly be used.

Figure 9:
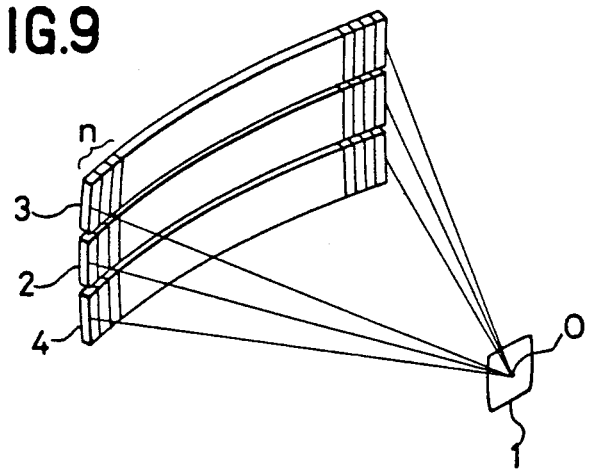
FIG. 9 is a diagram showing plural arrays, their scan planes and the intersection of scanning lines at the window in another embodiment of the present invention which employs plural linear arrays.
Figure 10:
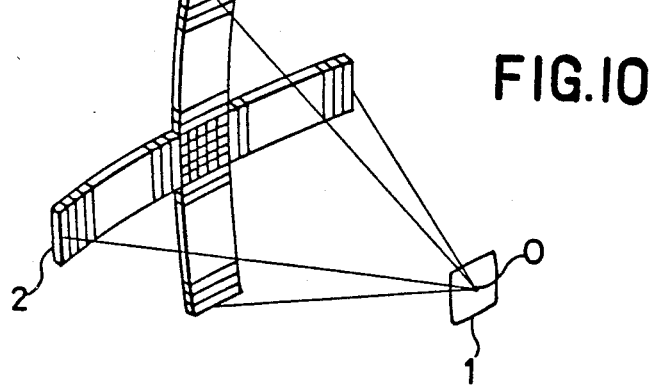
FIG. 10 is a diagram showing the mutually perpendicular two scan planes and the intersection of scanning lines at the window in another embodiment of the present invention which employs two perpendicularly intersecting linear arrays.
Figure 11:
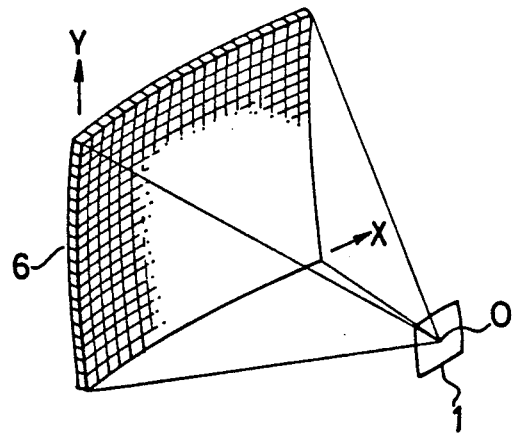
FIG. 11 is a diagram showing the three dimensional scanning and the intersection of scanning lines at the window in another embodiment of the present invention in which segments are arrayed in a matrix form on a spherical concave surface.

FIGS. 9 to 12 are schematic diagrams showing the relationships of the arrays, the scanning planes, the intersections of scanning lines and the windows in other embodiments of the present invention in which the array is formed multidimensionally or in plural linear arrays, and in which the scanning lines from the segment groups in the arrays are all made to intersect substantially at one point in the window or in its vicinity for performing the sector scan of at least two sections and/or three-dimensional sector scan. FIG. 9 shows an example using three linear arrays. FIG. 10 shows an example using two perpendicularly intersecting linear arrays and FIG. 11 shows an example using a matrix planar array. FIG. 12 is a sectional view illustrating the probe structure of FIG. 9. Reference numeral 1 indicates a window; 2 to 5 designate linear arrays; 6 identifies a matrix planar array; 13 denotes a sound absorber; and 14 represents a front space or room.

In FIG. 9, the three arc-shaped linear arrays 2, 3 and 4 are arranged on a sphere and substantially in parallel so that the center of curvature of the arc may lie at the window 1. The curvature of the arc can be slightly rearranged as required. In FIG. 9, the plane of the sector scan formed by the array 2 is set to perpendicularly intersect the plane of the window 1. The planes of sector scans formed by the arrays 3 and 4 pass through the center point O of the window 1 not perpendicularly but obliquely thereto. Accordingly, the arrays 3 and 4 appear to be parallel to each other in FIG. 9 but, in order for the planes of the sector scans formed by the arrays 3 and 4 to be spaced equally apart from the plane formed by the array 2, it is necessary to arrange the arrays 3 and 4 not in exact parallelism but in some deformed parallelism owing to the above-said oblique intersection. Each of the linear arrays 2, 3 and 4 can be provided by a conventional linear array used for diagnosing that is slightly curved to form a circular arc, and each consists of a number of narrow rectangular-shaped piezo electric PZT segments. Their operating method is the same as that of ordinary linear arrays. By selectively driving n adjacent elements as a group, an aperture is formed for beam convergence, and the beam center becomes a scanning line. The shift of the scanning line is performed by changing the positions of the group in the array. For example, by driving $n+1$ elements, a half-pitch deviated scanning line can be obtained, or by controlling the timing for transmission and reception according to the off-center distance of the segment in the group, and focus can be shifted electronically from being geometrically determined to being dynamically controlled along the depth. In this case, however, if the phase control is not effected, the focus point is defined by the geometrical arrangement at the center of curvature of the circular arc array. The convergence of the beam in the direction perpendicular to the scanning plane can be implemented by bending each rectangularly-shaped segment to be concave towards the emitting direction, or by placing in front of the array a columnar lens bent to conform to the arc of the linear array. Thus the techniques for ordinary linear arrays can be utilized. In FIG. 9 the center of curvature of the arc of each linear array is shown to coincide with the intersection point of the scanning lines and the intersection point is shown to coincide with the center 0 of the window 1, but it need not always be so.

FIG. 12 is a sectional view taken in the plane passing the center 0 of the window 1 and the center of the array 2 in FIG. 9, illustrating a specific probe structure.

The probe is formed to include circuit connections to the segments and the front room 14 having a substantially quadrangular pyramidal shape with its top end portion defined by the window 1. On the bottom of the quadrangular pyramid of the front room 14 are placed the linear arrays 2, 3 and 4. In practice, the interior surface of the front room 14, except the window 1, is entirely covered with or formed by the sound absorber 13. The front room 14 is filled with water, castor oil, liquid paraffin, fluorine oil or the like to form an ultrasonic wave propagating passage between the arrays 2, 3 and 4 and the window 1. The planes of sector scan formed by the arrays 2, 3 and 4 in the front room 14 pass through the center 0 of the window 1 and extend out therefrom point-symmetrically, forming three different planes of sector scan in the member under test. When the arrays 2, 3 and 4 are driven at the same frequency, they must be time shared. But if the arrays are operated at different frequencies, for example, 3.5 MHz for the array 2, 2.25 MHz for the array 3 and 1.5 MHz for the array 4, or at different CHIRP modulations, then the three arrays 2, 3 and 4 can be driven concurrently by discriminating received signals by filters, and the three planes can be scanned at the same time.

In FIG. 10, the arrays 2 and 5 are arranged so that their scan planes may perpendicularly intersect each other, and so that all the scanning lines may intersect in the neighborhood of the window 1 or at the point 0 on the window 1. At the intersecting portion of the arrays 2 and 5 the piezoelectric elements are not rectangularly-shaped but are arranged in a matrix form; they are connected in the vertical direction to form a part of the array 2 on one occasion and, on another occasion, they are connected in the lateral direction to form a part of the array 5. The arrays 2 and 5 are driven with different temporal phases so that when the matrix in their central intersecting portion is being activated as a part of either one of the arrays, the other array is driven in the other portion. The other arrangements, operation and scanning are identical with those in FIG. 9 and the planes of sector scan perpendicularly intersecting in the member under test can similarly be scanned in a time shared mode or operated entirely simultaneously.

In FIG. 11, the matrix planar array 6 is made up of segments arranged in a matrix form on a spherical plane having its center of curvature at the point O. In this case, since the segments in the vicinity of a given position on the X- and Y-axis can be selected as a group to a form a square, substantially circular or like aperture of a suitable opening, free three-dimensional sector scan can be performed.

FIGS. 13A and B and 14 illustrate specific examples of a double-layer array structure according to the present invention. FIGS. 13A and B show an example of a double-layer laminated linear array and FIG. 14 an example employing two perpendicularly intersecting double-layer linear arrays. Reference numerals 7, 8 and 10 indicate ultrasonic transducer segments and reference numer 13 identifies a sound absorber. In FIGS. 13A and B the vibrator arrays 7 and 8 are assembled into a multilayer structure forming two arcuate linear arrays. The vibrator array 7 comprises the piezoelectric elements 71, 72, 73, ... made for instance of PZT (zircon-lead titanate) of a center frequency 3.5 MHz. The vibrator array 8 has the organic piezoelectric plate 8' made for instance of PVDF (polyvinylidene fluoride) and its center frequency is adjusted to 2.25 MHz, for instance. The organic piezoelectric plate 8' has the signal electrodes 81, 82, 83, ... deposited over the area of its one side (on the front side in FIG. 13B showing a separated structure) and the grounding electrode 80 deposited over the entire area of the other side (on the back side in FIG. 13B). The piezoelectric segments 71, 72, 73, ... also each have thereon a signal electrode and a grounding electrode. Since the PZT is a ceramic material and inflexible, the piezoelectric segments 71, 72, 73, ... are produced one by one as independent segments, or they can be fabricated as a unitary structure by cutting thin grooves in a cylindrically shaped plate. The PVDF is flexible and the array 8 can be obtained by forming it in the form of a planar sheet and then bending it into an arc form. The sound absorber 13 made of a resinuous material mixed with a metal powder is provided in contact with the back of the array 7. The array 7, the sound absorber 13 and the array 8 are assembled together through using an adhesive binder. The PZT has an acoustic impedance of about $35 \times 10^6$ Kg/m² sec and the PVDF has an acoustic impedance of about $4 \times 10^6$ Kg/m² sec. Accordingly, it is preferable that the PZT and the PVDF resonate with $\lambda/2$ and $\lambda/4$ modes, respectively. Ultrasonic waves from the PZT pass through the PVDF. With the PVDF, it is also possible to produce an effect just like acoustic impedance matching with respect to the PZT. Ultrasonic waves emitted from the PVDF in the backward direction are mostly reflected by the PZT from the back to the front. In this example, the first and second layers are characterized by the center frequencies 3.5 and 2.25 MHz, respectively, but CHIRP modulation, pseudo-random code modulation or the like can also be employed. By discriminating received signals through using a filter, the two systems can be operated totally simultaneously. In this example, two linear arrays lie one on the other at the same position and the same plane can be scanned at different frequencies; therefore, this double-layer array structure is suitable for discriminating living tissues on the basis of the difference between their frequency characteristics.

In FIG. 14, the layer 7 of a linear array made of PZT and having a center frequency of 3.5 MHz and the layer 10 of a linear array made of PVDF and having a center frequency of 2.25 MHz are assembled together to overlap each other so that two perpendicularly intersecting planes of sector scan can be formed. In this case, the array 7 underlies the array 10. The reflector 11 is made of a material of the same acoustic impedance as that of the material of the array 7 and has the same thickness as does the array 7, and it reflects ultrasonic waves emitted in the backward direction from the array 10 so that the same characteristic provided for the intersecting portion of the arrays 7 and 10. The reflector 11 can be made of nonpolarized PZT ceramics or the like. The nonpolarized plates 12 are each made of a material of the same acoustic impedance as that of the material of the array 10 and have the same thickness as does the array 10 so that the ultrasonic waves emitted forward of the array 7 may become uniform over the entire area thereof, including the intersecting portion of the vibrator arrays 7 and 10. The nonpolarized plates 12 are each attached to the surface of the array 10 on either side of the intersecting portion. It is convenient to use, for the nonpolarized plates 12, PVDF employed for the array 10. According to this embodiment, it is possible to form two perpendicularly intersecting planes of sector scan through one window and to scan the planes simultaneously.

FIGS. 15A and B illustrate a specific example of an array structure for performing aperture control according to the present invention. Reference numerals 7 and 9 indicate arrays; 71, 72, 73 ... and 91, 92, 93, ... designate piezoelectric segments; and 90 identifies a grounding electrode. A sound field formed, for example, by a circular aperture of a radius "a" is beam-shaped and the beam radius in a near field is "a" but in a far field diverges in a sharp conical form with a vertical angle which is proportional to a/λ (where λ is the wavelength). Accordingly, when it is desired that beam patterns of two frequencies are made identical in the far field, the aperture "a" must be made proportional to the wavelength λ. In this case, however, the beam patterns in the near-field differ. According to the present invention, by determining the aperture so that the near field is mostly confined in the front room inside the window 1, beams in the member under test can be far-field beams. As a result of this, it is possible to obtain beams of the same pattern independent of the frequencies over the entire measurement depth range. This is important especially for discriminating living tissues through utilization of their frequency dependence. In FIG. 15A unit segments each composed of the piezoelectric segments such as 71 and 91 are arranged side by side linearly to form the arrays 7 and 9. The narrow rectangular-shaped piezoelectric segment 71 made of PZT is driven at a wavelength $\lambda_1$ and has an electrode on either side deposited over the entire length in the Y-axis direction and is effective along the entire length $W_1$. The piezoelectric element 91 is formed of PVDF is driven at a wavelength $\lambda_2$ and has a length $W_1$ in the Y-axis direction, but the effective length of its opposing electrodes is $W_2$, which bears such a relation as $W_1/W_2=\lambda_1/\lambda_2$. The front electrode of the piezoelectric element 91 is formed to extend to the lower end of the element 91 for serving as an electrode lead wire. Unit elements, each composed of the piezoelectric segments 71 and 91, are arranged side by side to form the arrays 7 and 9, which are formed as a unitary structure with the sound absorber 13, providing compounded linear arrays. In actual operation, $n_1$ and $n_2$ vibrators are selected from the arrays 7 and 9, respectively, to provide an aperture; in this case, $n_1/n_2=\lambda_1/\lambda_2$. With such an arrangement, beams substantially rectangular in cross section are formed but, in the far field, the beams of the wavelengths $\lambda_1$ and $\lambda_2$ become identical in shape with each other. In FIG. 15A the piezoelectric element 91 is shown with its portion above the point P of FIG. 15B taken off for convenience of display but, in practice, it is not removed.

FIG. 16 illustrates another specific example of the array structure which performs aperture control according to the present invention and which is shown to explain another aperture control of the linear array such as 8 in the Y-axis direction in FIGS. A and B. Reference numeral 8' indicates an organic piezoelectric sheet such as PVDF; 80 designates a grounding electrode; and 81, 82, 83, ... identify signal electrodes. The grounding electrode 8' has a width $W_2$ and is deposited on the organic piezoelectric plate 8' to extend the entire length thereof in the direction of its circular arc. By applying a voltage to the piezoelectric sheet while heated for polarization after forming such electrodes, it is possible to adapt the piezoelectric sheet so that only those portions thereof on which the grounding electrode 80 and the signal electrodes 81, 82, 83, ... face each other present a piezoelectric operation. The non-piezoelectric portion serves as a medium permitting the passage therethrough of ultrasonic waves from the piezoelectric elements 71, 72, 73, ... and is effective for preventing that the distribution of the ultrasonic waves from the piezoelectric elements 71, 72, 73, ... in the Y-axis direction is disturbed by that piezoelectric portion of the piezoelectric sheet 8' having the width $W_2$.

The foregoing description has been given of the principal part of the present invention for performing the three-dimensional sector-scan through utilization of linear arrays. Since the present invention does not involve phase control which is needed in the phased array, it is sufficient that the control circuit mainly perform selective switching of the segments, and hence it is simple and inexpensive. Furthermore, since the area for arrangement of transducer segments can be made wide, the segment array can easily be formed for three-dimensional scanning, multi-frequency operation and so forth, and its fabrication is easy and inexpensive.

On the other hand, the front room is required for intersecting the scanning lines at the window and, in order to prevent a bad influence of multiple reflection by the window, the skin surface, the transducer and so on, the following condition must be fulfilled.

$$l_1/v_1 \geq l_2/v_2$$

where $l_1$ is the path length between the transducer and the window, $V_1$ is the speed of sound in the medium in the front room, $l_2$ is a maximum measurement depth exterior the window and $v_2$ is the speed of sound in the member under test. This introduces the disadvantage that the front room becomes large. When $v_1 \approx v_2$, $l_1$ becomes at least equal to $l_2$ and, in the case of a heart or the like organ, $l_2$ is 18 cm, so that the probe becomes long. Letting the angle of scan in the member under test be represented by $\theta_2$, the angle of scan $\theta_1$ becomes, owing to refraction, as follows:

$$\sin\theta_1/\sin\theta_2 = v_1/v_2$$

When $v_1 \approx v_2$, if $2\eta_2 = 90°$, then $2\theta_1 = 90°$ and, $l_2 = 18$ cm, the probe becomes too big for practical use. For actual use of the probe, it is absolutely necessary to reduce the length $l_1$ and the angle of scan $2\theta_1$ in the front room (the vertex angle of the outer shape of the guadrangular pyramidal probe). This requirement can be met by selecting, as a medium in the front room, a medium satisfying $v_1/v_2 \leq 1$. This is evident from the abovesaid expressions for $l_1$ and $\theta_1$. It is very preferable that $v_1/v_2 \leq \frac{1}{2}$. The speed of sound $v_2$ is 1500 m/sec in the living tissue or the like, whereas the sound speed $v_1$ is 700, 527 and 590 m/sec in available flourinated oil materials such as FC48, FC72 and FC75 available from 3M Inc., respectively, providing an excellent $v_1/v_2$ ratio.

It will be apparent that many modifications and variations may be effected without departing from the scope of the novel concepts of the present invention.

What is claimed is:

1. An ultrasonic sector-scan probe comprising:
    at least a first array of a respective plurality of ultrasonic transducer segments arranged to form an arc of a circle, for transmitting and receiving ultrasonic waves;

a window for transmitting and receiving said ultrasonic waves, said window being disposed in the vicinity of the center of said arc;

an ultrasonic wave propagation medium filled in a front room defined between each said array and the window;

a converging acoustic lens provided in the vicinity of said window for providing a focal region for said ultrasonic waves over a measuring depth range in a subject under test which is held in contact with the exterior of said window; and means for sequentially driving different groups of said transducer segments in each said array, with respective different phases for the respective transducer segments of each said group, so that ultrasonic waves emitted from each said group are formed into a respective beam for transmission along a respective scanning line at a respective angle into said subject under test, and focused in said front room, between said lens and said transducer segments in the vicinity of said lens and at a point spaced from said lens;

wherein each said beam is further focused in said subject under test, respective reflected waves from the subject are received through the window, and said scanning lines of the respective groups all intersect substantially at one point in the vicinity of said window to perform sector scanning of the subject under test.

2. The probe of claim 1, wherein the ultrasonic wave propagation medium filled in the front room is a medium in which the speed of sound is substantially lower than the speed of sound in the subject under test.

* * * * *

UNITED STATES PATENT AND TRADEMARK OFFICE
CERTIFICATE OF CORRECTION

PATENT NO. : 4,580,451

DATED : 8 April 1986

INVENTOR(S) : HIROHIDE MIWA et al

It is certified that error appears in the above-identified patent and that said Letters Patent is hereby corrected as shown below:

Col. 1, line 23, "avoding" should be --avoiding--;

Col. 1, line 67, "donotes" should be --denotes--;

Col. 1, line 68, after "space" insert --or--.

Col. 3, line 13, "can not" should be --cannot--;

Col. 3, line 68, after "above" insert --,--.

Col. 5, line 34, delete "the" (second occurrence).

Col. 6, line 15, ";" shoud be --,--.

Col. 8, line 3, after "Accordingly," insert --in--.

Col. 9, line 15, "te" should be --the--,

Col. 9, line 41, "a = $\theta_2$ = $\theta_1$ = 0 ," should be --a = $\theta_2$ - $\theta_1$ = 0 --.

Col. 10, line 3, "array" should be --arrays--;

Col. 10, line 44, "piezo electric" should be --piezoelectric--;

Col. 10, line 54, after "and" insert --the--;

Col. 10, line 62, "ly-shaped" should be --ly shaped--.

UNITED STATES PATENT AND TRADEMARK OFFICE
CERTIFICATE OF CORRECTION

PATENT NO. : 4,580,451

DATED : 8 April 1986

INVENTOR(S) : HIROHIDE MIWA et al

It is certified that error appears in the above-identified patent and that said Letters Patent is hereby corrected as shown below:

Col. 11, line 35, "rectangularly-" should be --rectangularly--.

Col. 13, line 35, "PVDF" should be --PVDF,--;

Col. 13, line 59, "Figs A and B" should be --Figs. 13A and B--.

Col. 14, line 45, "$V_1 \approx V_2$ if $2n_2$" should be --$V_1$ is approximately equal to $V_2$, if $2\theta_2$--.

Signed and Sealed this

Second Day of September 1986

[SEAL]

Attest:

DONALD J. QUIGG

Attesting Officer

Commissioner of Patents and Trademarks